US005632971A

United States Patent [19]

Yang

[11] Patent Number: 5,632,971

[45] Date of Patent: May 27, 1997

[54] EMPTY MEDICINAL AND FOOD CAPSULE

[75] Inventor: Joo H. Yang, Seoul, Rep. of Korea

[73] Assignee: Su Heung Capsule Co., Ltd., Kyong gi-do, Rep. of Korea

[21] Appl. No.: 587,705

[22] Filed: Jan. 19, 1996

[30] Foreign Application Priority Data

Sep. 23, 1995 [KR] Rep. of Korea .................. 1995-26161

[51] Int. Cl.$^{6}$ .................................................. A61K 9/48

[52] U.S. Cl. ....................... 428/34.1; 428/35.7; 428/36.9; 428/132; 428/134; 424/453; 424/454; 53/900; 220/4.21

[58] Field of Search .................................. 428/34.1, 35.7, 428/36.9, 132, 134; 424/451, 452, 453, 454; 53/900; 206/528, 530; 220/4.21, 4.24

[56] References Cited

U.S. PATENT DOCUMENTS

| | | | |
|---|---|---|---|
| 2,718,980 | 9/1955 | Strom | 206/528 |
| 3,664,495 | 5/1972 | Graham et al. | 206/530 |
| 4,040,536 | 8/1977 | Schwarz | 204/530 |
| 4,196,565 | 4/1980 | Bodenmann et al. | 53/900 |
| 4,792,451 | 12/1988 | Kim | 424/453 |
| 4,822,618 | 4/1989 | Schweiger et al. | 424/453 |
| 5,223,265 | 6/1993 | Wong | 424/453 |
| 5,501,857 | 3/1996 | Zimmer | 424/451 |

*Primary Examiner*—Ellis Robinson
*Assistant Examiner*—Rena L. Dye
*Attorney, Agent, or Firm*—Birch, Stewart, Kolasch & Birch, LLP

[57] ABSTRACT

An empty medicinal and food capsule includes a cap member containing a cap circumferential slot disposed on the upper portion and at least one raised member disposed on the inner surface thereof, the cap circumferential slot having a triangular slot formed on the outer surface thereof, and a body member containing a body circumferential slot disposed on the upper portion thereof whereby the cap member and the body member can be slidably locked with each other by slidably locking the cap circumferential slot with the body circumferential slot, at the time, the triangular slot prevents from semi-locking or final locking in a prelocking state, and prevents from separating the cap member form the body member in a final locking state, and the capsule is not deformed.

7 Claims, 3 Drawing Sheets

EMPTY MEDICINAL AND FOOD CAPSULE

BACKGROUND OF THE INVENTION

1. Field of the Invention

The present invention relates to empty medicinal and food capsules and more particularly, to improved medicinal and food capsules having a plurality of triangular slots formed on the inner surface of a cap circumferential slot of a cap member for preventing the semi-locking or final locking in a prelocking state, and for preventing the separation of the cap member from the body member in a final locking state so as to facilitate mass-production by utilizing an automatic filing apparatus. Also, the cap member and the body member are preliminarily locked prior to final locking, and the capsule is not deformed.

2. Description of the Related Art

There are many types of medicinal capsules which are well known in art comprising a cap having a cap circumferential slot and a raised member and a body which may or may not have a body circumferential slot. However, these capsules suffer from a number of deficiencies such as, for example, since such capsules as known in the prior art, for example as shown in FIGS. 8 and 9 comprise a cap A including a cap circumferential slot and a raised member d, and a body B having a tapered mouthpiece e, when the capsule is preliminarily locked in an atmosphere of moisture, heat, etc., the capsules can be transformed in the direction indicated by the arrows and changed in dimension as shown by the dotted lines (FIG. 9). As shown in the prior art of FIGS. 10, 11(A) and 11(B), such capsules comprise a cap including a cap circumferential slot and a raised member $g_1$, and a body B including a body circumferential slot $g_2$, whereby the raised member $g_1$ is slidably locked to the body circumferential slot $g_2$ of the body B. However, when the capsule is preliminarily locked in a moist or hot atmosphere, the capsule can be readily transformed from the capsule as shown in FIG. 11(A) to the capsule as shown in FIG. 11(B). As will be noted, the labels of the cap A and the body B do not match when the capsule changes its dimension.

Accordingly, the present applicant has developed an improvement in the empty medicinal capsule as disclosed in U.S. Pat. No. 4,792,451 entitled "Medicinal Capsule" which comprises a cap member containing a first circumferential slot formed on the outer surface of the upper portion, at least one raised member formed on the inner surface of the cap, a body member containing a second circumferential slot formed on the outer surface of the upper portion thereof for slidably locking with the first circumferential slot of the cap member during final locking, and at least one connecting member formed on the outer surface of the second circumferential slot of the body member and extending internal of the body member for slidably locking with the raised member of the cap member. The raised member and the connecting member are dimensioned relative to each other so as to form a space therebetween whereby when the cap member and body member are preliminarily locked prior to final locking, and the capsule is not deformed. However, in the pre-locking state, the capsule is semi-locked or finally locked and sometimes, the cap member is separated from the body member in a final sealing state.

SUMMARY OF THE INVENTION

Accordingly, it is an object of the present invention to provide an improved empty medicinal and food capsule, which eliminates the above problems encountered with the conventional medicinal capsules.

Another object of the present invention is to provide an empty medicinal and food capsule which includes a cap member having a cap circumferential slot which contains a plurality of triangular slots formed on the inner surface of the cap circumferential slot, and a body member having a body circumferential slot, whereby the capsules prevented from semi-locking or final locking in a preliminary lock state prior to final locking, and the cap member is prevented from easily separating from the body member in a final locked state so as to be readily mass-produced by utilizing an automatic printing machine and an automatic filing machine.

A further object of the present invention is to provide an improved medicinal capsule having the cap and body members in alignment so that the label printed thereon are also in alignment.

Still another object of the present invention is to provide an empty medicinal and food capsule which is simple in structure, inexpensive to manufacture, durable in use, and refined in appearance.

Other objects and further scope of applicability of the present invention will become apparent from the detailed description given hereinafter. It should be understood, however that the detailed description and specific examples, while indicating preferred embodiments of the invention, are given by way of illustration only, since various changes and modifications within the spirit and scope of the invention will become apparent to those skilled in the art from this detailed description.

Briefly described, the present invention is directed to an empty medicinal and food capsule which includes a cap member containing a cap circumferential slot disposed on the upper portion and at least one raised member disposed on the inner surface thereof, the cap circumferential slot having a triangular slot formed on the outer surface thereof, and a body member containing a body circumferential slot disposed on the upper portion thereof whereby the cap member and the body member can be slidably locked with each other by slidably locking the cap circumferential slot with the body circumferential slot. At this time, the triangular slot prevents semi-locking or final locking in a prelocking state, and prevents the separation of the cap member from the body member in a final locking state, with the capsule not being deformed.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
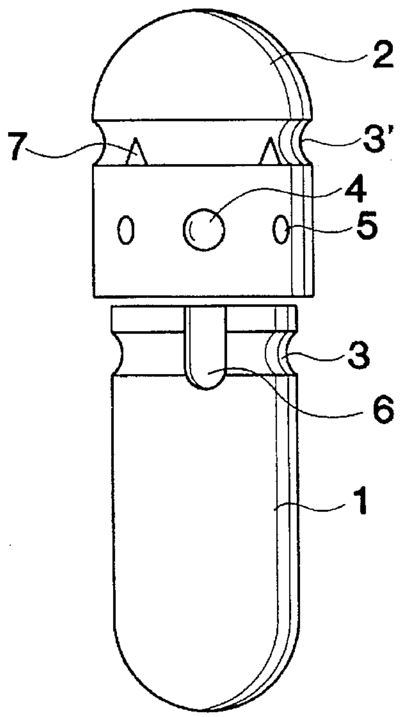
FIG. 1 is an exploded front side elevational view of an empty medicinal food capsule as defined by the present invention; B
Figure 2:
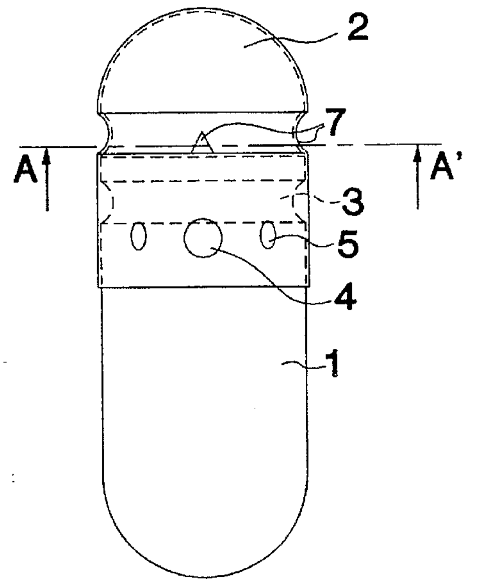
FIG. 2 is a front side elevational view of the prelocking of the cap member and the body member of the present invention.

Referring now in detail to the drawings for the purpose of illustrating preferred embodiments of the present invention, the empty medicinal and food capsule as shown in FIGS. 1, 2 an 5 comprises a body member 1 including a body circumferential slot 3 formed on the outer surface of the lower portion thereof and a vertical air outlet channel 6 which crosses the body circumferential slot 3. A cap member 2 including a cap circumferential slot 3' is formed on the outer surface of the upper portion of the capsule. At least one raised member 4 and at least one auxiliary raised member 5 is formed on the inner surface thereof providing a prelocking state and for use in preventing the transformation or movement of the capsule. The raised member 4 is preferably two and the auxiliary raised member 5 is preferably four.

Figure 3:
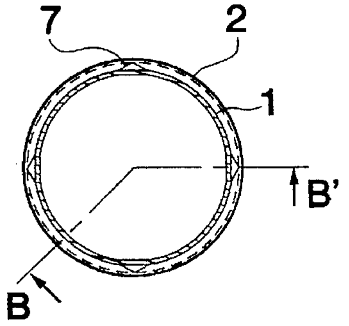
FIG. 3 is a cross-sectional view, taken along line A—A' of FIG. 2.
Figure 4:
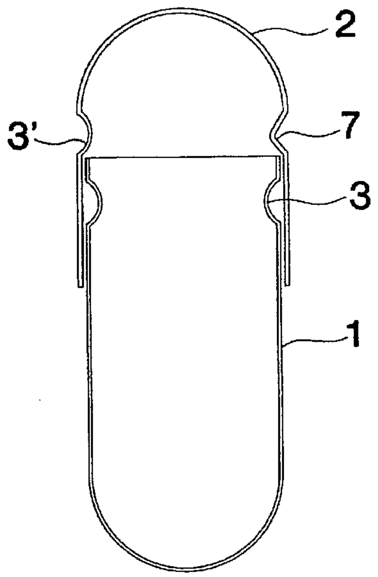
FIG. 4 is a cross-sectional view, taken along line B—B' of FIG. 3.
Figure 5:
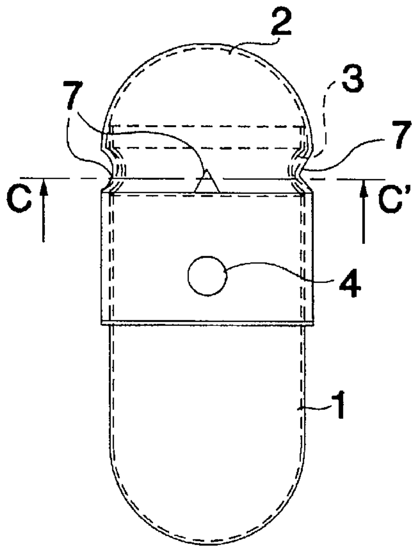
FIG. 5 is a front side elevational view of the final locking of the cap member and the body member of the present invention.
Figure 6:
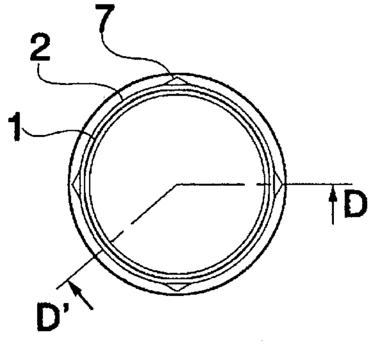
FIG. 6 is a cross-sectional view, taken along line C—C' of FIG. 5.
Figure 7:
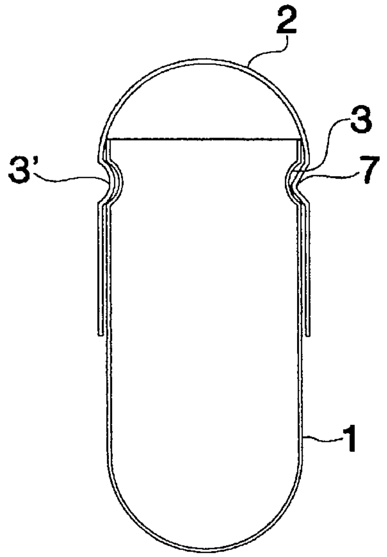
FIG. 7 is a cross-sectional view, taken along line D—D' of FIG. 6.
Figure 8:
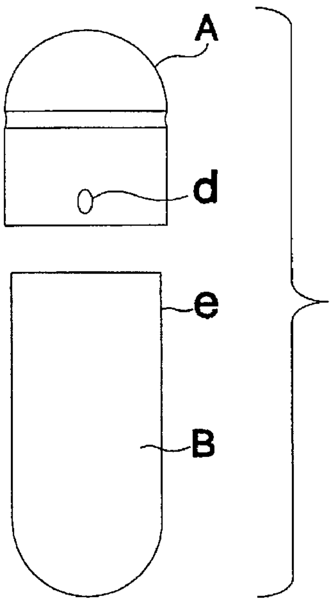
FIG. 8 CONVENTIONAL ART
FIG. 8 is a front side elevational view of a conventional medicinal capsule.
Figure 9:
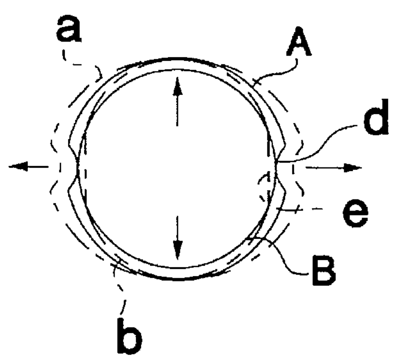
FIG. 9 CONVENTIONAL ART
FIG. 9 is a cross-sectional view of FIG. 8.
Figure 10:
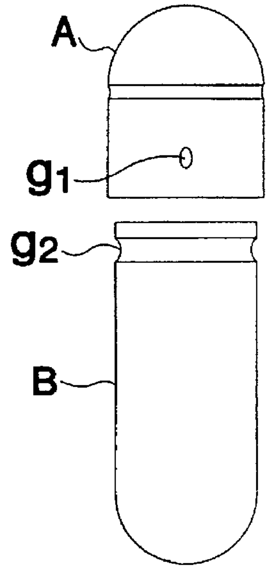
FIG. 10 CONVENTIONAL ART
FIG. 10 is a front side elevational view of another conventional medicinal capsule.
Figure 11A:
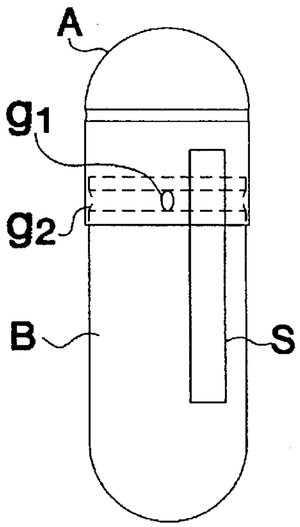
FIG. 11(A) CONVENTIONAL ART
FIG. 11(A) is a front side elevational view of FIG. 10, showing a label in alignment.
Figure 11B:
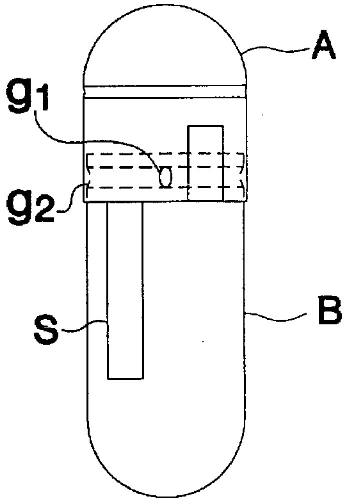
FIG. 11(B) CONVENTIONAL ART
FIG. 11(B) is a front side elevational view of FIG. 10, showing the label out of alignment due to the transformation thereof.

As shown in FIGS. 2, 3 and 4, the cap circumferential slot 3' is provided with a plurality of raised triangular slots 7 formed on the inner surface of the cap member 2 whereby upon prelocking, when the cap is placed on the lower portion of the capsule, the cap is stopped at the circumferential slot 3' by the plurality of raised triangular slots 7, thus affectively maintaining the prelocking state so that there is no semi-locking or final locking of the capsule. As seen in FIGS. 5, 6 and 7, upon final locking, since the plurality of triangular slot 7 is supporting the body circumferential slot 3, the body and cap members 1 and cannot separate from each other. Preferably, the plurality of raised triangular slot 7 are three to six in number.

The empty medicinal and food capsules according to the present invention can be assembled as follows. When the body member 1 and the cap member 2 are preliminary locked before holding the medicine or food to the capsule e.g. "prelocking", the raised member 4 and the auxiliary raised members 5 of the cap member 2 lock in a position below the body circumferential slot 3 (FIG. 2). Therefore the shape of the body member 1 is not transformed or twisted, and the body member 1 and the cap member 2 can be readily prelocked.

In addition, since the plurality of raised triangular slots 7 acts as a stop at the circumferential end disposed over the body circumferential slot 3, the medicinal and food capsules of the present invention can be readily mass-produced by utilizing an automatic printing apparatus and an automatic high-speed filing apparatus. Furthermore, the medicinal and food capsule of the present invention does not produce a semi-locking product or a final locking product even though exterior pressures applied to the capsule during printing, selection and air transportation steps.

After filling the capsules, when the final locking is accomplished, the body circumferential slot 3 of the body member 1 and the cap circumferential slot 3' are locked to each other. At this time the circumferential slot 3 is tightly braised by the plurality of raised triangular slots 7 as shown in FIGS. 6 and 7 so as to more strongly lock the body and cap members 1 and 2 together. Since each raised triangular slots 7 is inwardly raised, the braising power to the body circumferential slot 3 of the body member 1 is very strong.

The invention being thus described, it will be obvious that the same may be varied in may ways. Such variations are not to be regarded as a departure from the spirit and scope of the invention, and all such modifications as would be obvious to one skilled in the art are intended to be included in the scope of the following claims.

What is claimed is:

1. A medicinal and food capsule having inside and outside surfaces, thereof, said capsule comprising:

a body member and a cap member, said cap member being adapted to slidably fit over said body member to form a completed capsule, said body member containing a body circumferential slot formed on said outside surface of the upper portion thereof, said cap member containing a cap circumferential slot formed on said outside surface thereof, a plurality of projections formed on said inside surface of the cap member at the cap circumferential slot and extending inwardly for engaging an upper end of the body member above the body circumferential slot to form a prelocking state, and for tightly braising said body circumferential slot in a final locking state, and a plurality of raised members disposed on the lower portion of said cap member and extending inwardly from the inside surface of said cap member, whereby the body member and cap member are preliminarily locked prior to final locking, the medicinal and food capsule is not deformed, and the cap member is not separated from the body member.

2. The medicinal and food capsule of claim 1, wherein said projections are triangular slots.

3. The medicinal and food capsule of claim 2, wherein the plurality of projections are three to six in number.

4. The medicinal and food capsule of claim 1, wherein said plurality of raised members include at least one main raised member and at least two auxiliary raised members.

5. The medicinal and food capsule of claim 4, wherein said main raised member is two in number.

6. The medicinal and food capsule of claim 4, wherein said auxiliary raised member is four in number.

7. The medicinal and food capsule of claim 1, wherein said body member further contains a vertical air outlet channel which crosses the body circumferential slot for removing air as a medicinal and food product is introduced into the capsule.

* * * * *